United States Patent [19]
Sereboff

[11] Patent Number: 5,141,489
[45] Date of Patent: Aug. 25, 1992

[54] CERVICAL BRACE

[76] Inventor: Joel L. Sereboff, 2215 Millridge Rd., Owings Mills, Md. 21117

[21] Appl. No.: 736,589

[22] Filed: Jul. 26, 1991

[51] Int. Cl.⁵ .............................................. A61F 5/08
[52] U.S. Cl. ................................... 602/18; 128/380; 128/DIG. 23
[58] Field of Search ................. 128/76 R, 75, 87 B, 128/DIG. 23, DIG. 20, 380, 402, 399, 403; 602/17, 18

[56] References Cited

U.S. PATENT DOCUMENTS

| | | | |
|---|---|---|---|
| 1,964,962 | 7/1934 | Rosenblum | 128/DIG. 23 X |
| 2,735,424 | 2/1956 | Benjamin | |
| 3,667,457 | 6/1972 | Zumaglini | |
| 3,901,225 | 8/1975 | Sconu | 128/402 X |
| 4,383,523 | 5/1983 | Schurman | |
| 4,823,776 | 4/1989 | Foster et al. | |
| 4,905,997 | 3/1990 | Last | 128/402 X |
| 5,005,374 | 4/1991 | Spitler | 128/402 X |
| 5,020,536 | 6/1991 | Keen | 128/402 |
| 5,027,801 | 7/1991 | Grim | |
| 5,050,595 | 9/1991 | Krafft | 128/402 X |

FOREIGN PATENT DOCUMENTS 165720 9/1953 Australia .

Primary Examiner—Richard J. Apley
Assistant Examiner—Linda C. M. Dvorak
Attorney, Agent, or Firm—Morton J. Rosenberg; David I. Klein

[57] ABSTRACT

This invention provides a cervical brace (10) for substantial immobilization of a user's head (14). The cervical brace (10) of the subject invention includes a head immobilization mechanism (24) for interface with the chin of the user (12). Additionally, a rear immobilization mechanism (26) is provided for contacting the occipital portion of the user's head (14). The immobilization mechanisms (24 and 26) are provided with rigid plate members (28 and 26) in combination with flexible sheets (32 and 42) to form pockets within which flexible pad members (36 and 38) may be removably inserted. In this manner, the user's head (14) is maintained in a substantially immobile positioning location while dispersing the loads over a wider area to minimize any user discomfort.

9 Claims, 2 Drawing Sheets

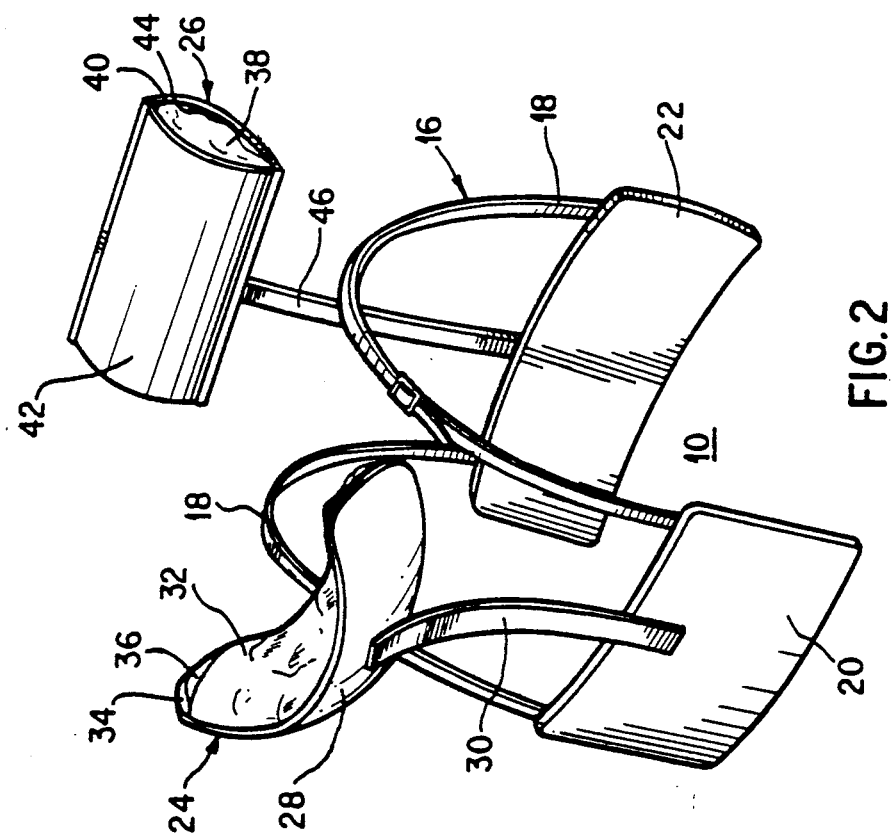
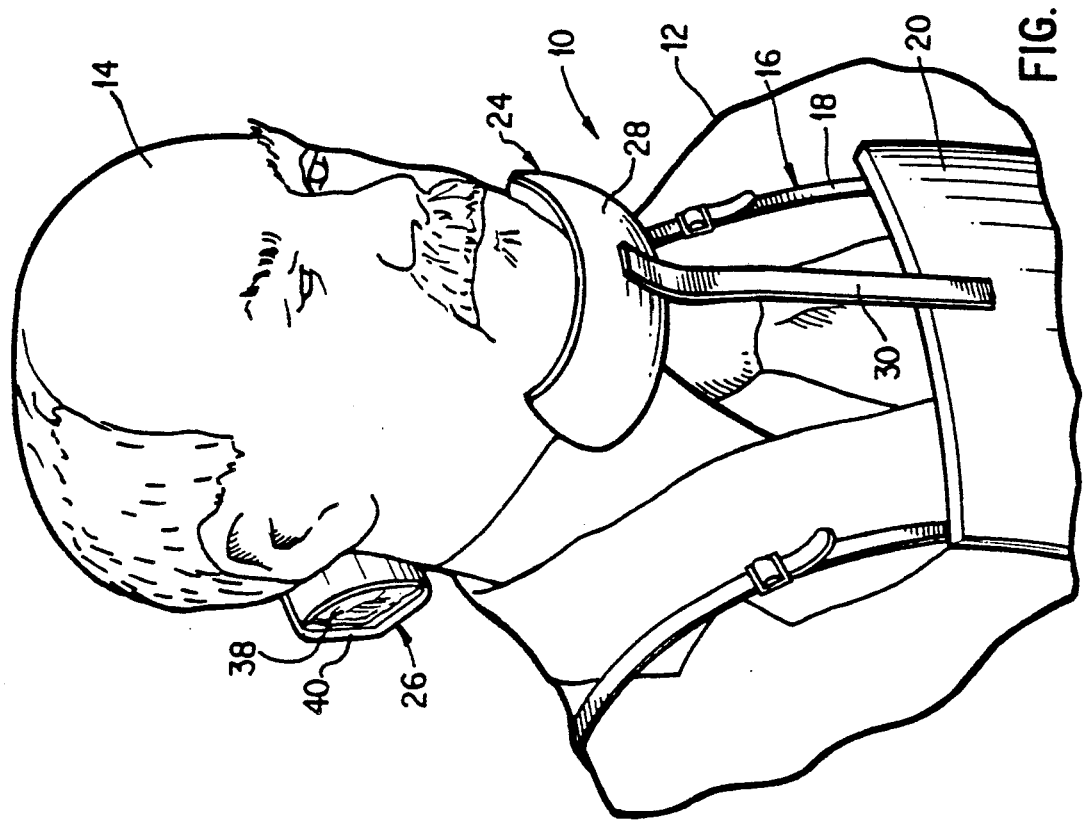
FIG. 2
FIG. 1

CERVICAL BRACE

BACKGROUND OF THE INVENTION

1. Field of the Invention

This invention relates to improvements in cervical braces. In particular, this invention directs itself to a cervical brace wherein the contact area between the user's head and the rigid portions of the cervical brace are provided with deformable elements. More in particular, this invention relates to a cervical brace having a rigid head support mechanism within which is removably insertable a pouch containing a substantially liquid or gel-like composition which deforms upon loading by the forces applied to the user's head. Still further, this invention directs itself to a cervical brace wherein the immobilizing rigid support includes a pocket section for insert of a deformable pouch or container for interface with the user's head.

2. Prior Art

Cervical braces are well-known in the art. However, in prior art systems, the support mechanism is generally a rigid support which may cause discomfort to the user when the cervical brace is being used over a long period of time. In such prior art systems, there is a large amount of discomfort on the part of the user and various bruises and abrasions may result from the use of such prior art cervical braces.

In some prior art cervical braces, such may be formed of a somewhat flexible support mechanism, however, such is not removable at the discretion of the user, or the medical authorities.

The best prior art known to Applicant includes U.S. Pat. Nos. 3,308,491; 4,576,150; 4,913,755; 4,710,991; 4,671,267; 4,668,564; 4,243,041; 4,520,801; 4,955,368; 4,854,306; 4,712,540; 3,850,164; 4,708,129; and, 4,034,747.

In some prior art, such as that shown in U.S. Pat. No. 3,308,491, there are provided cushioning structures which include gel compositions. However, such do not provide for the insert of such gel compositions into the pocket of a cervical collar for the purposes and objectives, as is described by this invention concept. In other prior art systems, such as that shown in U.S. Pat. No. 4,576,150, such provide for an orthopedic support for the head and neck with pad elements spaced apart from each other and connected by tapes. Once again, this does not provide for the insertable deformable containers as provided in the subject invention concept when taken in combination with the rigid support mechanism of the subject cervical brace.

SUMMARY OF THE INVENTION

A cervical brace is provided for releasable attachment to the body of a user for supporting the user's head. The cervical brace includes a mounting mechanism for the cervical brace to the body of the user. Additionally, a mechanism is provided for substantially immobilizing the user's head when the cervical brace is mounted on the user's body. The immobilization mechanism is fixedly secured to the mounting mechanism of the cervical collar. A mechanism is provided for resiliently positioning the user's head with respect to the immobilization mechanism and the resilient positioning mechanism is removably insertable into the immobilization mechanism.

BRIEF DESCRIPTION OF THE DRAWINGS

FIG. 1 is a perspective view of the cervical brace of the present invention showing the positioning of the cervical brace on the body of the user;

FIG. 2 is a perspective view of the cervical brace according to the present invention; and, FIG. 3 is a perspective view, partially cut-away of a portion of the head immobilization and flexible positioning mechanism of the subject cervical brace.

DESCRIPTION OF THE PREFERRED EMBODIMENTS

Figure 3:
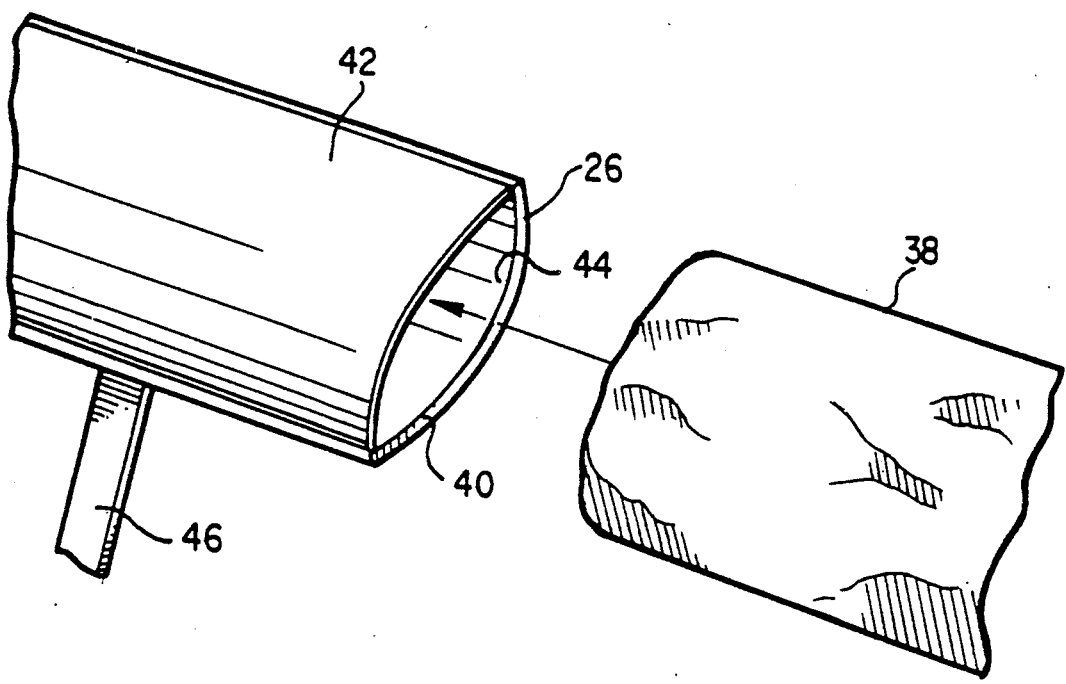

Referring now to FIGS. 1-3, there is shown cervical brace 10 for releasable attachment to the body of user 12 for supporting and substantially immobilizing the user's head 14 in a predetermined position responsive to medical requirements. In general, cervical brace 10 of the subject invention concept provides for a substantially immobilizing mechanism while providing additional comfort to user 12 during times when the user's head 14 contiguously interfaces with elements of cervical brace 10. In the manner to be described in following paragraphs, the user's head portions which have a force loading component applied thereto by cervical brace 10 interfaces with portions of cervical brace 10 to allow deformation and distribute the force loading over a larger surface area in order to provide a more comfortable fit. As will be seen in following paragraphs, where a rigid structure is necessary for immobilization of the user's head 12, deformable elements of cervical brace 10 may be removed in a simple and efficient manner.

Referring now to FIG. 2, cervical brace 10 includes mounting mechanism 16 for mounting cervical brace 10 to the body of user 12. Although shown in one form for the purposes of illustration and description, mounting mechanism 16 may take a wide variety of forms which are commercially found in the marketplace. In particular, mounting mechanism 16 of the subject invention concept includes harness straps 18 which are fixedly secured on opposing ends to thoracic plate member 20 on one end and back plate member 22 on opposing ends thereof. Thoracic plate member 20 in use contiguously interfaces with the chest portion of user 12 in order to distribute loading forces and maintain cervical brace 10 in a relatively fixed position on user 12. Additionally, back plate member 22 interfaces with the back of user 12 to similarly provide for stabilization of other elements of cervical brace 10, as will be described in following paragraphs. Thoracic plate member 20 and back plate member 22 may be arcuate in contour to readily adapt to the contour of a person's chest and back sections. Additionally, thoracic plate member 20 and back plate member 22 may be formed of a metal composition or some like rigid composition not important to the inventive concept as herein described, with the exception that the particular compositions of members 20 and 22 are sufficiently rigid to accept the loads applied and maintain their structural integrity.

Referring to FIGS. 1 and 2, cervical brace 10 further includes chin support mechanism 24 having a generally arcuate contour for contiguous interface with the user's chin. Chin support mechanism 24 includes frontal chin rest plate member 28 being generally arcuate in contour for interfacing with the contours of the user's chin as shown in FIG. 1. Frontal chin rest plate 28 may be formed of a rigid metal construction composition. In general, such composition may be formed of steel, aluminum, or some like composition not important to the inventive concept as herein described, with the exception that the rigid composition forming frontal chin rest plate member 28 is structurally able to accept the loads applied. Frontal chin rest plate 28 is rigidly secured to thoracic plate member 20 by frontal support member 30 which may be welded upon opposing ends or otherwise rigidly secured to frontal chin rest plate member 28 and thoracic plate member 20, as shown.

Chin support mechanism 24, includes chin rest flexible sheet 32 and is secured to chin rest plate member 28 in an overlying manner throughout a portion of a periphery of chin rest plate member 28 providing open portion 34 defining a pocket formed between an inner surface of frontal chin rest plate member 28 and chin rest flexible sheet 32. Within the pocket, there may be inserted frontal chin rest resilient pad member 36.

Chin rest resilient pad member 36 may be similar, if not identical, in construction to head rest resilient pad member 38 as shown in FIG. 3. Frontal chin rest resilient pad member 36 may be removably sandwiched between chin rest flexible sheet 32 and an inner surface of frontal chin rest plate member 28.

Releasable securement between frontal chin rest plate member 28 and chin rest flexible sheet 32 may be attained through a number of well-known fastening mechanisms such as hook and loop type fasteners, or snap buttons.

Frontal chin rest resilient pad member 36 and head rest resilient pad member 38 may be a fluidly sealed resilient pouch containing a substantially fluid composition. The fluid composition within frontal chin rest resilient pad member 36 may be of a gel-like viscosity, or in the alternative, may be a liquid such as water. The important concept being that upon loading forces being applied to resilient pouch or frontal chin rest resilient pad member 36, that such is deformable to allow dispersement of the load applied by the chin of the user over a wide area and thus provide for less discomforture on the part of user 12 when in contiguous interfacing contact with chin support mechanism 24.

Frontal chin rest resilient pad or pouch member 36 may include a covering of a closed cell plastic composition such as polyethylene, or some like composition.

Head support mechanism 26 includes head rest member 40 for contacting the back of the head of user 12, as shown in FIG. 1. Head rest plate member 40 may be formed of a rigid metallic composition such as steel, or some like material similar to frontal chin rest plate member 28. Additionally, rear support member 46 is rigidly secured on opposing ends to head rest plate member 40 and back plate member 22 through welding or some other fixed securement technique.

Head support mechanism 26 further includes head rest flexible sheet 42 which is fixedly secured to head rest plate member 40 throughout a portion of the periphery of head rest plate member 40. Opening 44 is provided for insert of head rest resilient pad member 38 and such is clearly seen to be sandwiched between head rest flexible sheet 42 and head rest plate member 40.

As was the case with frontal chin rest resilient pad member 36, head rest resilient pad member 38 may form a sealed pouch which is closed upon its periphery and is fluid tight. A liquid or liquid-like substance, such as a gel, is contained within head rest resilient pad or pouch member 38 to allow for deformation of pouch or pad member 38 upon loading of the back of head user 12. In this manner, forces applied to the user's head 14 are dispersed over a large surface area and provides less discomfort on the part of user 12 during prolonged contiguous interface with chin support mechanism 24 and head support mechanism 26.

Chin support mechanism 24 and head support mechanism 26 in combination provide for the mechanism of substantially immobilizing user's head 14 when cervical brace 10 is mounted on the user's body, as has previously been described.

Thus, the combination of chin support mechanism 24 and head support mechanism 26 provides for the mechanism of immobilizing the user's head 14 when cervical brace 10 is mounted on the user's body. Pouches or sealed containers 36 and 38 provide for resilient positioning of user's head 14 with respect to the immobilization mechanisms 24 and 26 with both of the pouches 36 and 38 being removably insertable into immobilization mechanisms 24 and 26.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A cervical brace for releasable attachment to a body of a user for supporting the user's head comprising:

means for mounting said cervical brace to the body of the user, said mounting means including a thoracic plate and a back plate;

means for substantially immobilizing the user's head when said cervical brace is mounted on the user's body, said immobilization means fixedly secured to said mounting means, said means for immobilization including (1) a rigid chin rest plate member having an arcuate contour for contiguous interface with the user's chin, said rigid chin rest plate member being rigidly coupled to said thoracic plate, (2) a first flexible sheet secured to said chin rest plate member throughout a predetermined portion of a periphery of said chin rest plate member with a remaining portion being unsecured to define an opening to a chin rest pocket formed therebetween, (3) a rigid head rest plate member having an arcuate contour for contiguous interface with the back of the user's head, said head rest plate member being rigidly coupled to said back plate, and (4) a second flexible sheet secured to said head rest plate member throughout a predetermined portion of a periphery of said head rest plate member with a remaining portion being unsecured to define an opening to a head rest pocket formed therebetween;

a chin rest resilient pad member removably disposed within said chin rest pocket for resilient interface with the chin of the user, said chin rest resilient pad member being formed by a first sealed resilient pouch containing a substantially fluid composition; and, a head rest resilient pad member removably disposed within said head rest pocket for resilient and deformable interface with the head of the user, said head rest resilient pad member being formed by a second sealed resilient pouch containing a substantially viscous fluid composition.

2. The cervical brace as recited in claim 1 where said substantially fluid composition of said chin rest resilient pad member is water for providing deformation of said sealed resilient pouch when said sealed resilient pouch interfaces with the chin of the user.

3. The cervical brace as recited in claim 1 where said substantially fluid composition of said chin rest resilient pad member is a gel composition for providing deformation of said sealed resilient pouch when said sealed resilient pouch interfaces with said chin of the user.

4. The cervical brace as recited in claim 1 where said first flexible sheet is formed of a textile composition.

5. The cervical brace as recited in claim 1 where said frontal chin rest member is formed of a metal composition.

6. The cervical brace as recited in claim 1 where said opening of said chin rest pocket is releasably closeable for capturing said chin resilient pad member therein 7. The cervical brace as recited in claim 1 where said second sealed resilient pouch includes a pouch covering formed of a closed cell plastic composition.

8. The cervical brace as recited in claim 7 where said head support member is formed of a substantially rigid metal composition.

9. The cervical brace as recited in claim 8 where said second flexible sheet is releasably closeable for capturing said head rest resilient pad member.

* * * * *